(12) United States Patent
Kodama et al.

(10) Patent No.: US 6,480,736 B1
(45) Date of Patent: Nov. 12, 2002

(54) METHOD FOR DETERMINING BASAL METABOLISM

(75) Inventors: Miyuki Kodama, Tokyo; Hitoshi Sato, Tsurugashima, both of (JP); Steven B. Heymsfield, Mount Kisco, NY (US)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/920,298

(22) Filed: Aug. 2, 2001

Related U.S. Application Data

(60) Provisional application No. 60/228,767, filed on Aug. 30, 2000.

(51) Int. Cl.[7] .................................................. A61B 5/00
(52) U.S. Cl. ...................................................... 600/547
(58) Field of Search ................................. 600/300, 547, 600/587

(56) References Cited

U.S. PATENT DOCUMENTS

| 5,415,176 A | * | 5/1995 | Sato et al. .................... 600/547 |
| 5,611,351 A | * | 3/1997 | Sato et al. .................... 600/547 |
| 6,088,615 A | * | 7/2000 | Masuo .......................... 600/547 |
| 6,198,964 B1 | * | 3/2001 | Oguma ......................... 600/547 |
| 6,256,532 B1 | * | 7/2001 | Cha .............................. 600/547 |

* cited by examiner

*Primary Examiner*—Max Hindenburg
(74) *Attorney, Agent, or Firm*—McDermott, Will & Emery (57) ABSTRACT

Basal metabolism is determined by obtaining an age of a subject; determining fat-free mass of the subject; and calculating the basal metabolism of the subject using the determined fat-free mass and a reciprocal of the age. The basal metabolism can be calculated using the formula represented by BMR=A×FFM+B×(1/age)+C, in which BMR is basal metabolism (kcal/day), FFM is fat-free mass (kg), and A, B, and C are constants.

6 Claims, 10 Drawing Sheets

METHOD FOR DETERMINING BASAL METABOLISM

RELATED APPLICATIONS

This application claims priority from U.S. Provisional Patent Application Ser. No. 60/228,767, filed Aug. 30, 2000.

FIELD OF THE INVENTION

The present invention relates to determining basal metabolism of a patient, and more particularly, to a method for determining basal metabolism using fat-free mass.

BACKGROUND OF THE INVENTION

Expensive and extensive apparatus are usually necessary to determine accurate basal metabolism of a subject. Additionally, many loads and measuring conditions are required, and a subject has to keep at rest for a long time with wearing a facemask and a mouthpiece. In addition, only a specialist can handle the measuring apparatus and evaluate the measured results. As such, the general public can hardly perform their own tests to obtain an accurate measure of their own basal metabolism.

For these reasons, a statistically standard basal metabolism value is used in most cases to determine basal metabolism. The statistically standard basal metabolism value is obtained, for example in Japan, by multiplying a reference value of basal metabolism on the basis of gender and age according to Health Service Bureau of Ministry of Health and Welfare by body weight. This standard value is used despite the importance of a relationship between adiposis and basal metabolism.

Figure 1:
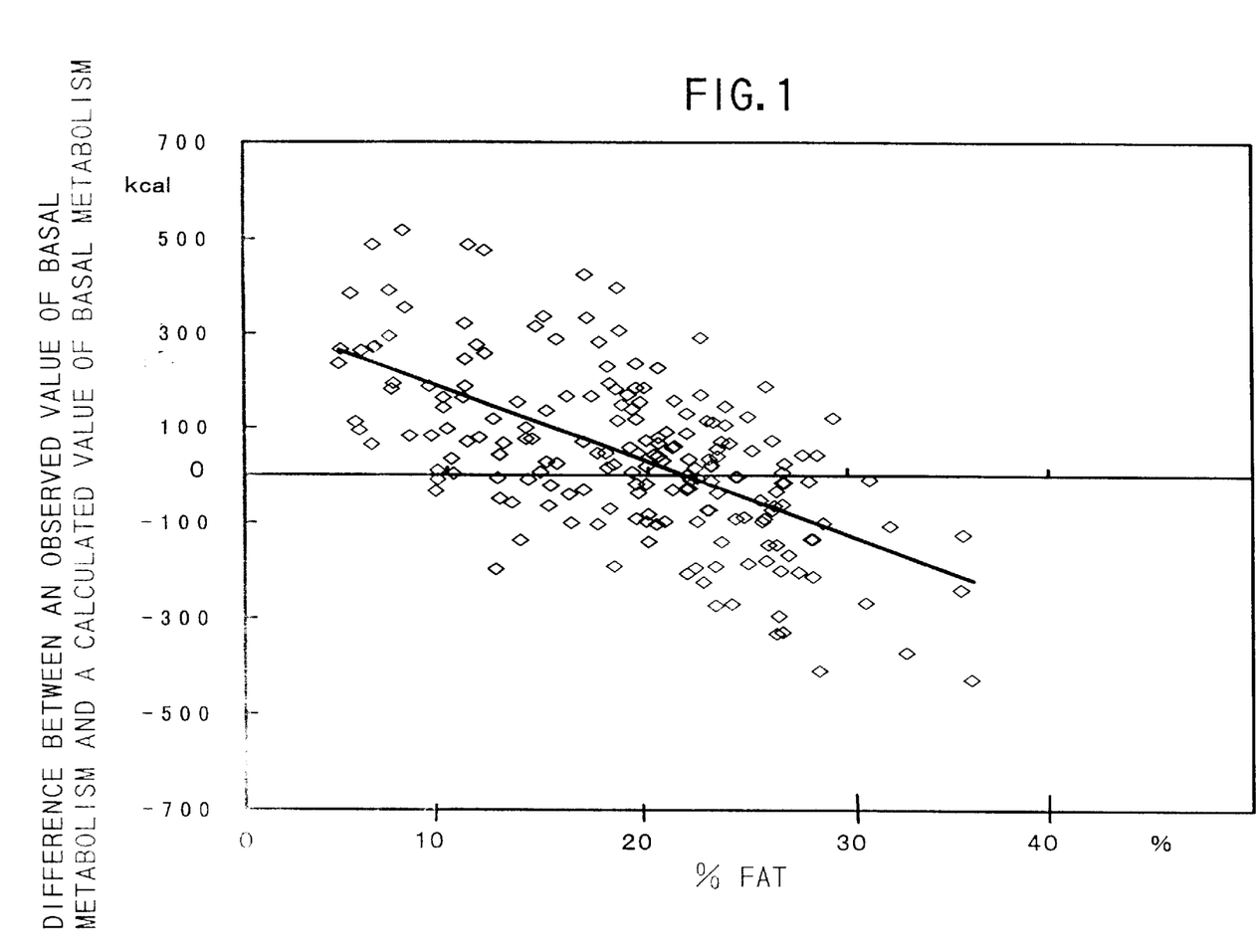
FIG. 1 is a graph showing a relationship between difference between an observed value of basal metabolism and a calculated value of basal metabolism and a fat rate.

Basal metabolism, however, is considered to be directly proportional to fat-free mass rather than to actual body weight. As shown in FIG. 1, the basal metabolism determined using the above-mentioned method is suitable for a human having a standard body build and a standard body composition, because body composition is a strong effective factor. However, a calculated value of basal metabolism tends to be higher than an observed value of basal metabolism in a pycnic type (i.e., a human with a high fat rate) who has a heavy body weight and a large amount of fat. Also, a calculated value of basal metabolism tends to be lower than an observed value of basal metabolism in a slim and muscular man (i.e., a human with a low fat rate). Therefore, the above-mentioned method for calculating basal metabolism is not preferable from the viewpoint of guidance for adiposis.

Since basal metabolism has a close relation to the fat-free mass, a formula represented as follows is employed in a foreign nutrition science academy.

$$BMR = A \times FFM + B$$

Figure 2:
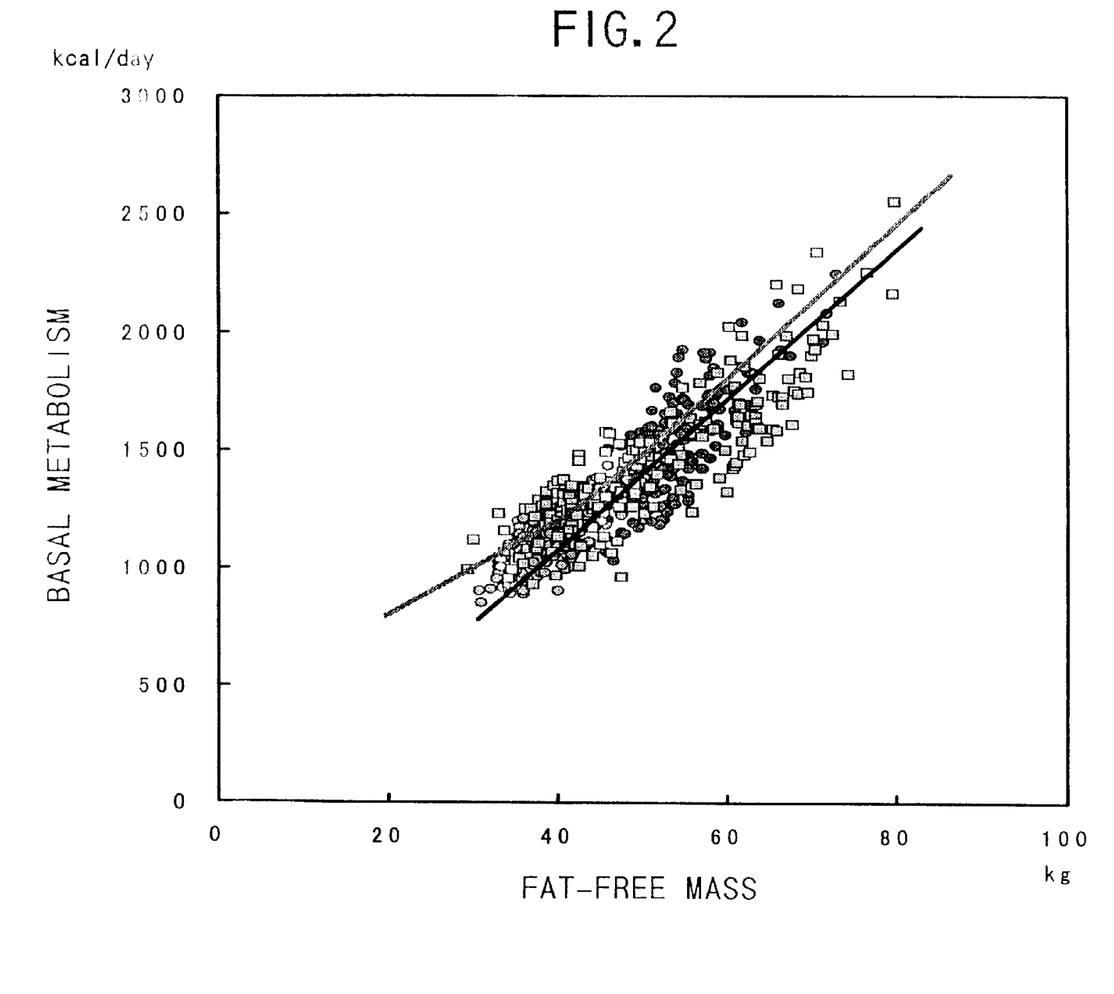
FIG. 2 is a graph showing a relationship between fat-free mass and basal metabolism.

BMR is basal metabolism (kcal/day), FFM is fat-free mass (kg), and A and B are constants. The relationship between the basal metabolism and the fat-free mass is shown in FIG. 2. This formula produces a correlation coefficient of 0.824, which shows the formula closely correlates with observed results. However, the basal metabolism obtained with the above mentioned formula is adapted to adults but not to children in a growth period. In addition, the calculated value with the formula tends to be lower than an observed value in a person having a low fat-free mass, especially in young slim females according to the measured results by the present inventors. Accordingly, a need exists for an improved apparatus for calculating basal metabolism that provides a calculated value that more accurately correlates with the observed value of basal metabolism so that guidance can be effectively provided as to diet and exercise for a pycnic type person and also to children.

SUMMARY OF THE INVENTION

These and other needs are met by embodiments of the present invention which provide a method for determining basal metabolism. The method includes obtaining an age of a subject; determining fat-free mass of the subject; and calculating the basal metabolism of the subject using the determined fat-free mass and a reciprocal of the age. By adding the reciprocal of an age as a factor in determining basal metabolism, in addition to fat-free mass, the present invention improves the accuracy of an arithmetic method used to determine basal metabolism.

In an aspect of the present invention, basal metabolism can be determined using the formula represented by $BMR = A \times FFM + B \times (1/age) + C$, in which BMR is basal metabolism (kcal/day), FFM is fat-free mass (kg), and A, B, and C are constants.

In accordance with another aspect of the present invention, the method can determine basal metabolism using the formula represented by $BMR = A \times FFM^2 + B \times FFM + C \times (1/age) + D$, in which BMR is basal metabolism (kcal/day), FFM is fat-free mass (kg), and A, B, C, and D are constants.

In an additional embodiment, the method includes obtaining an age and a body weight of a subject; determining fat-free mass of the subject; and determining basal metabolism of the subject using the determined fat-free mass, the body weight, and a reciprocal of the age. By adding both age and weight as factors in determining basal metabolism, in addition to fat-free mass, the present invention improves the accuracy of an arithmetic method used to determine basal metabolism.

In an aspect of the invention, the basal metabolism can be determined using the formula represented by $BMR = A \times FFM + B \times (1/age) + C \times body\ weight + D$, in which BMR is basal metabolism (kcal/day), FFM is fat-free mass (kg), and A, B, C, and D are constants.

In another aspect of the invention, the basal metabolism is calculated with a formula represented by $BMR = A \times FFM^2 + B \times FFM + C \times (1/age) + D \times body\ weight + E$, in which MR is basal metabolism (kcal/day), FFM is fat-free mass (kg), and A, B, C, D, and E are constants.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DETAILED DESCRIPTION OF THE INVENTION

Figure 3:
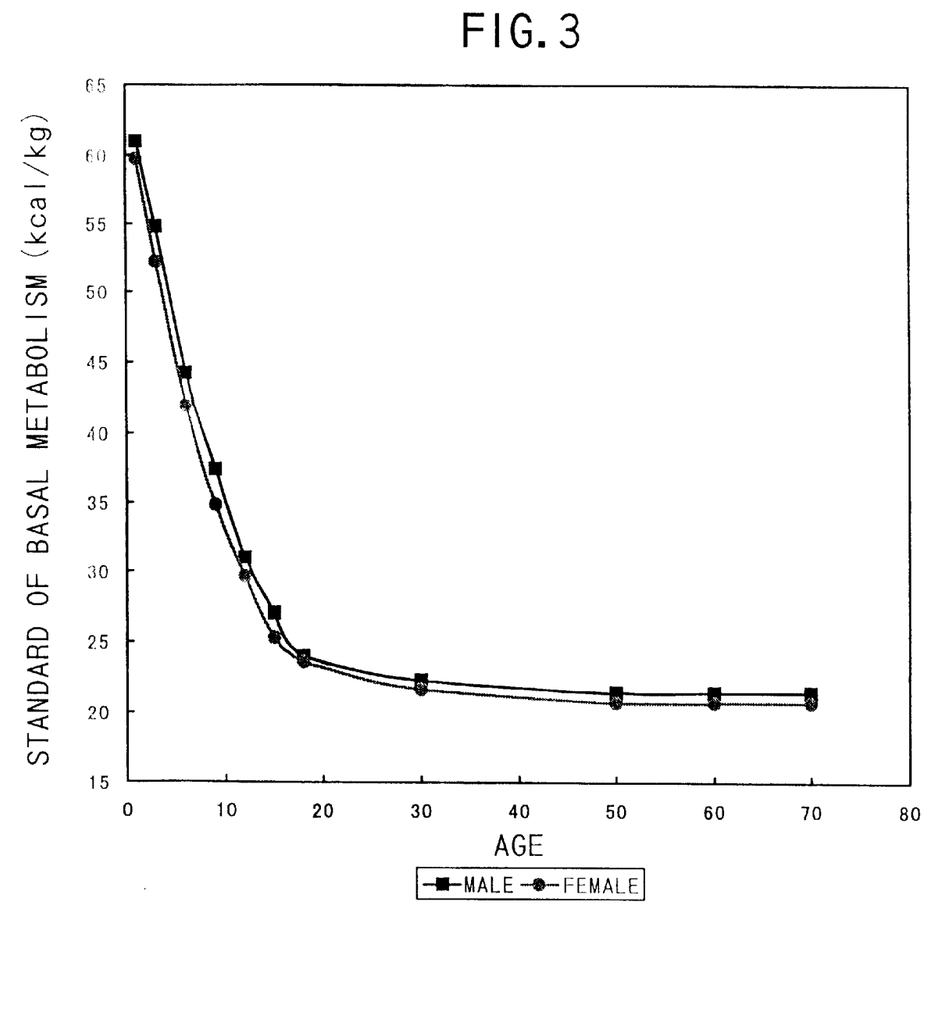
FIG. 3 is a graph showing a relationship between an age and a reference value of basal metabolism.
Figure 4:
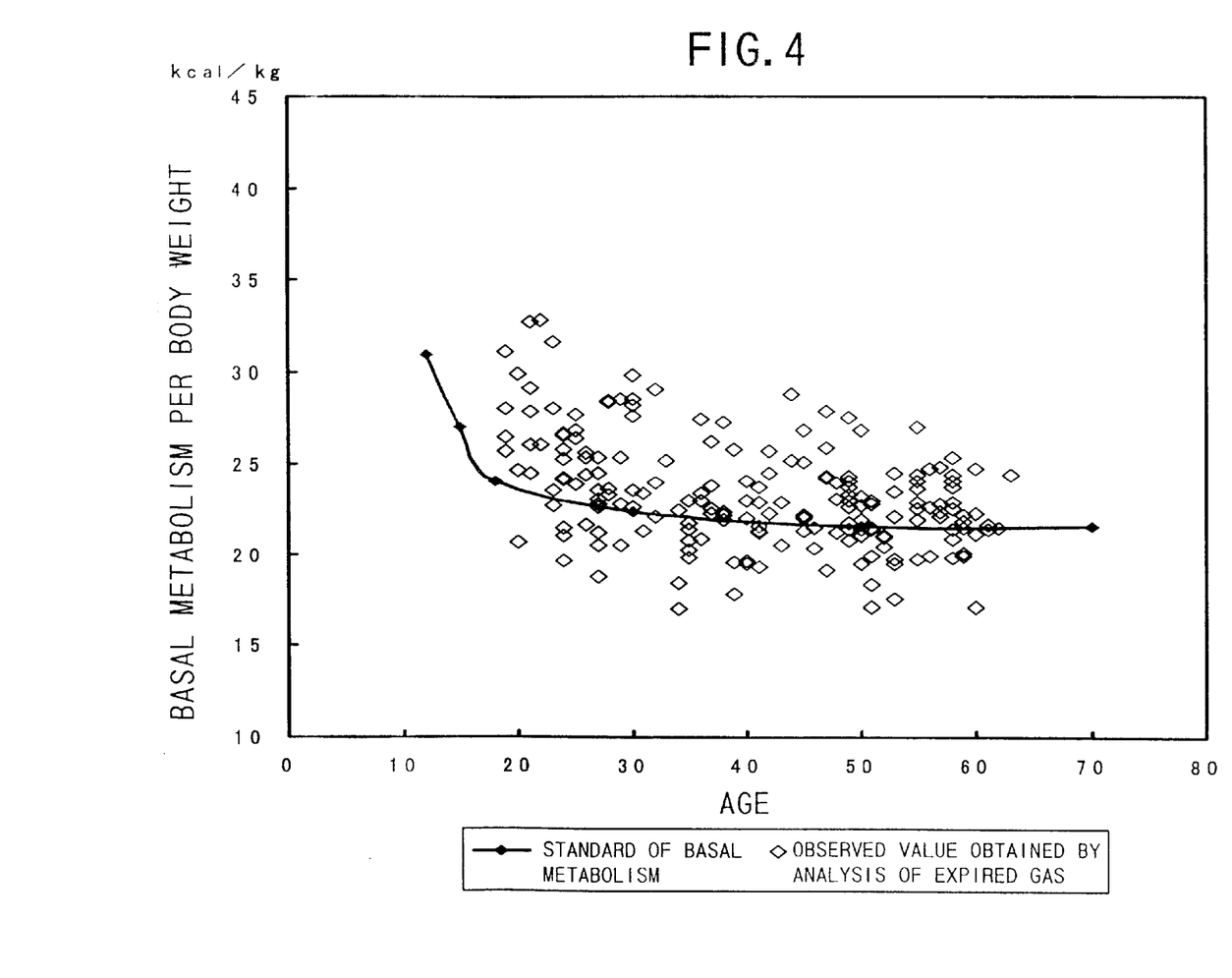
FIG. 4 is a graph showing a relationship between basal metabolism per body weight and an age.

An embodiment of the present invention will be described with reference to the figures. As shown in FIG. 3, the inventors of the present invention have reviewed the values of basal metabolism provided by the Health Service Bureau of Ministry of Health and Welfare and have determined that these values are inversely proportional to age of the subject. In addition, as illustrated in FIG. 4, the inventors of the present invention have independently observed that basal metabolism per body weight is inversely proportional to an age. Furthermore, the inventors have of the present invention have found that a reciprocal of an age in addition to fat-free mass is preferably utilized when calculating basal metabolism. Accordingly, the inventors have found that the basal metabolism can be calculated using the formula represented by $BMR = A \times FFM + B \times (1/age) + C$, in which BMR is basal metabolism (kcal/day), FFM is fat-free mass (kg), and A, B, and C are constants. It should be understood, however, that the formula is not limited to using metric measuring system values and can use any type of measuring system values.

Figure 5:
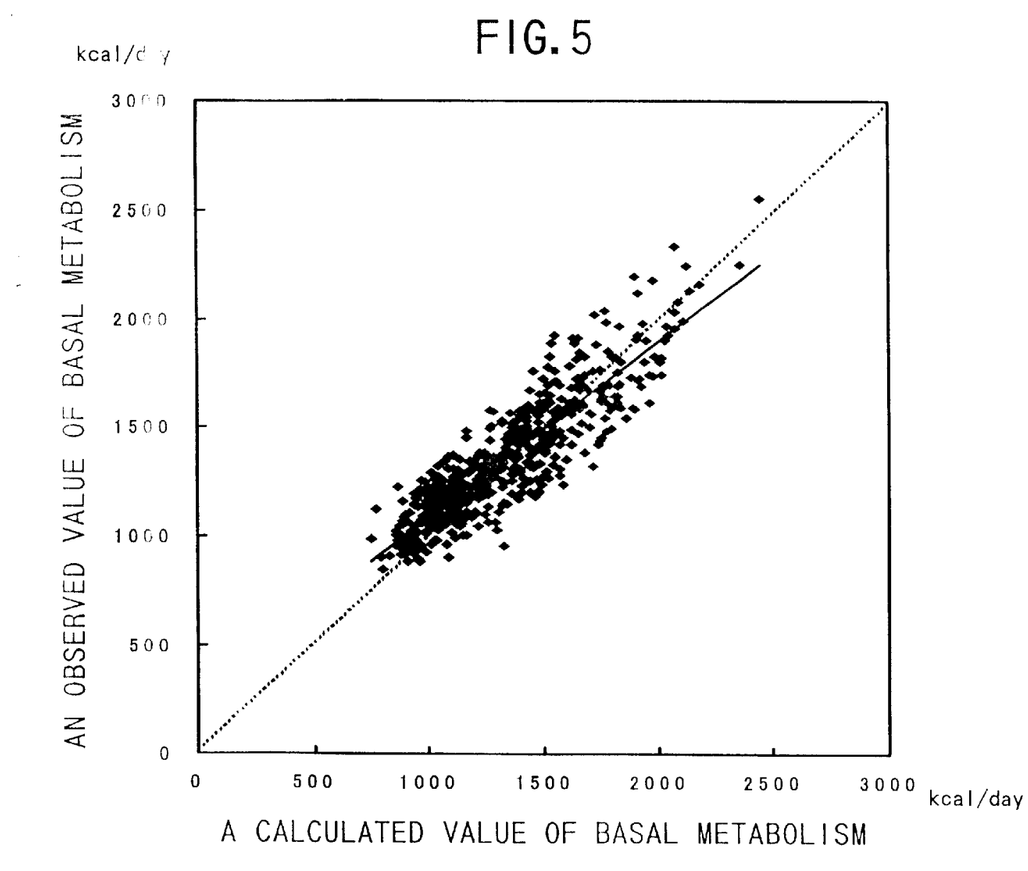
FIG. 5 is a graph showing a relationship between a calculated value of basal metabolism and an observed value of basal metabolism.
Figure 6:
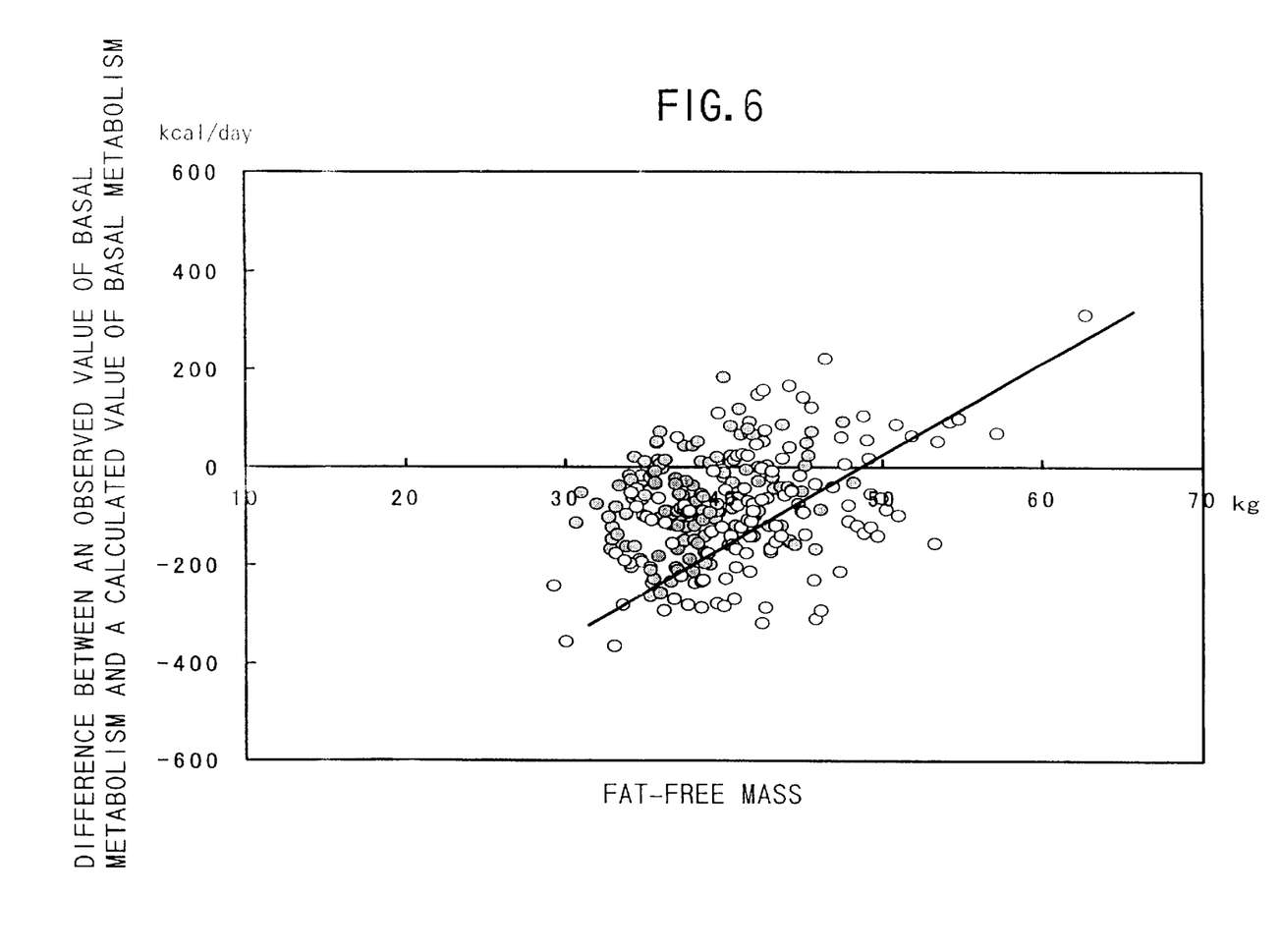
FIG. 6 is a graph showing a relationship between difference between an observed value of basal metabolism and a calculated value of basal metabolism and fat-free mass.

As shown in FIG. 5, a correlation coefficient between the basal metabolism obtained using the above mentioned formula and the observed basal metabolism is 0.870. The observed value was obtained by analysis of expired gas. As shown in FIG. 6, the difference between an observed value and a calculated value against fat-free mass is half of the conventional data.

As shown in FIG. 2, a calculated value of basal metabolism tends to be lower than an observed value in humans with extremely low fat-free mass. The inventors of the present invention have found that a reciprocal of an age and squared thereof in addition to fat-free mass is preferably utilized when calculating basal metabolism. Accordingly, the inventors have found that the basal metabolism can be calculated using the formula represented by $BMR = A \times FFM^2 + B \times FFM + C \times (1/age) + D$, in which BMR is basal metabolism (kcal/day), FFM is fat-free mass (kg), and A, B, C, and D are constants. It should be understood, however, that the formula is not limited to using metric measuring system values and can use any type of measuring system values.

Figure 7:
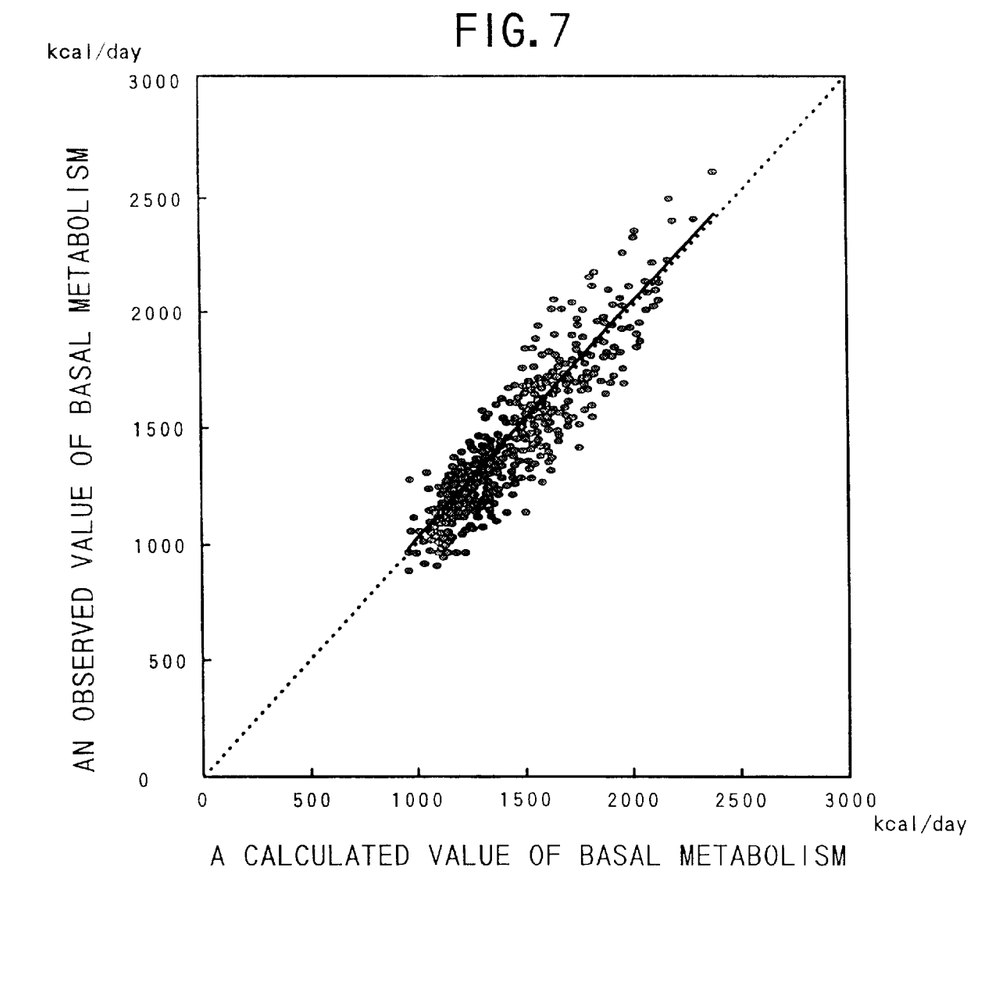
FIG. 7 is a graph showing a relationship between a calculated value of basal metabolism and an observed value of basal metabolism.
Figure 8:
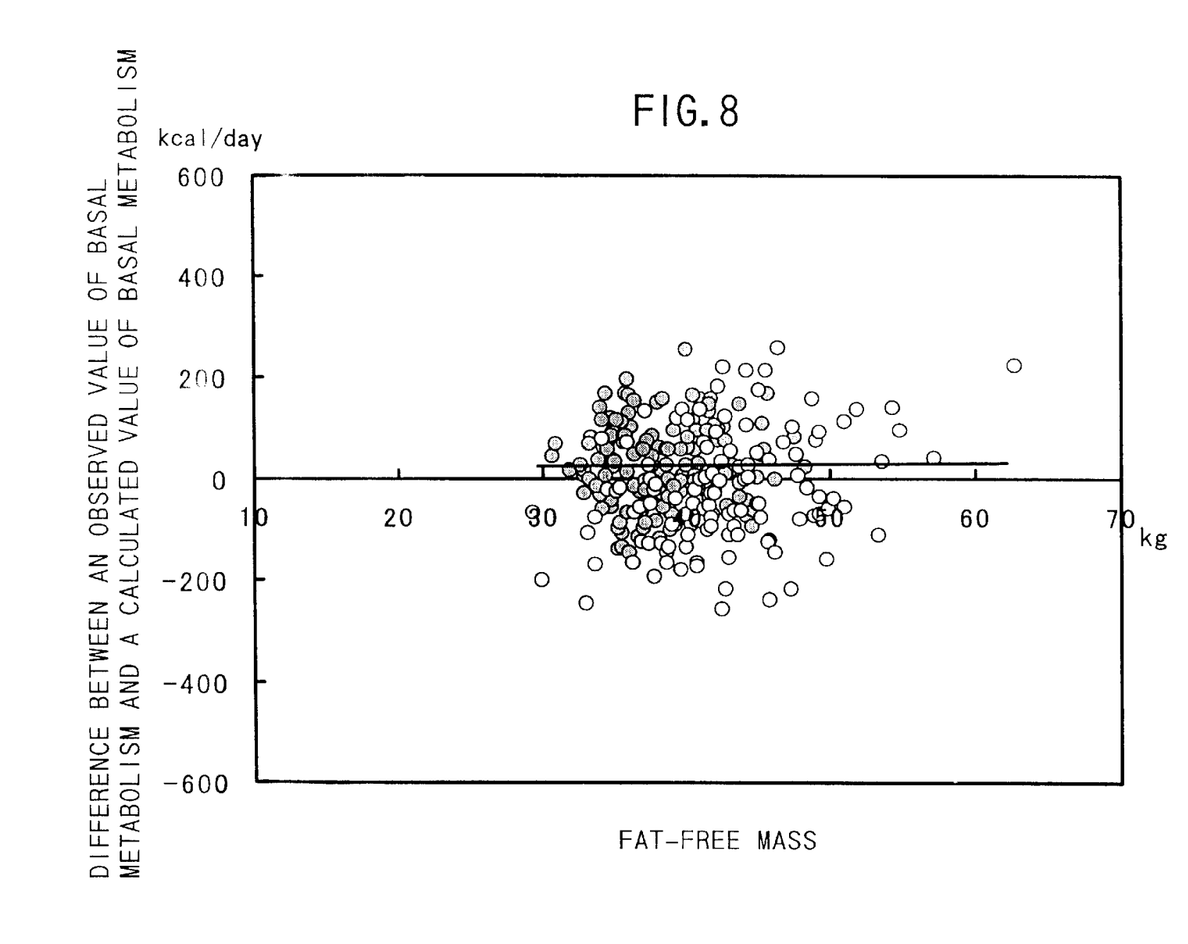
FIG. 8 is a graph showing a relationship between difference between an observed value of basal metabolism and a calculated value of basal metabolism and fat-free mass.

As shown in FIG. 7, a correlation coefficient between the basal metabolism obtained using the above mentioned formula and the observed basal metabolism is 0.88. The observed value was obtained by analysis of expired gas. As shown in FIG. 8, the difference between an observed value and a calculated value against fat-free mass is almost identical.

The inventors of the present invention recognize that the calculated value of basal metabolism tends to be lower than an observed value thereof in humans with low fat-free mass, especially in young slim female and in children. As such, the inventors of the present invention have found that a reciprocal of an age and body weight in addition to fat-free mass is preferably utilized to calculate basal metabolism. Accordingly, the inventors have found that the basal metabolism can be calculated using the formula represented by $BMR = A \times FFM + B \times (1/age) + C \times body\ weight + D$, in which BMR is basal metabolism (kcal/day), FFM is fat-free mass (kg), and A, B, C, and D are constants. It should be understood, however, that the formula is not limited to using metric measuring system values and can use any type of measuring system values.

Figure 9:
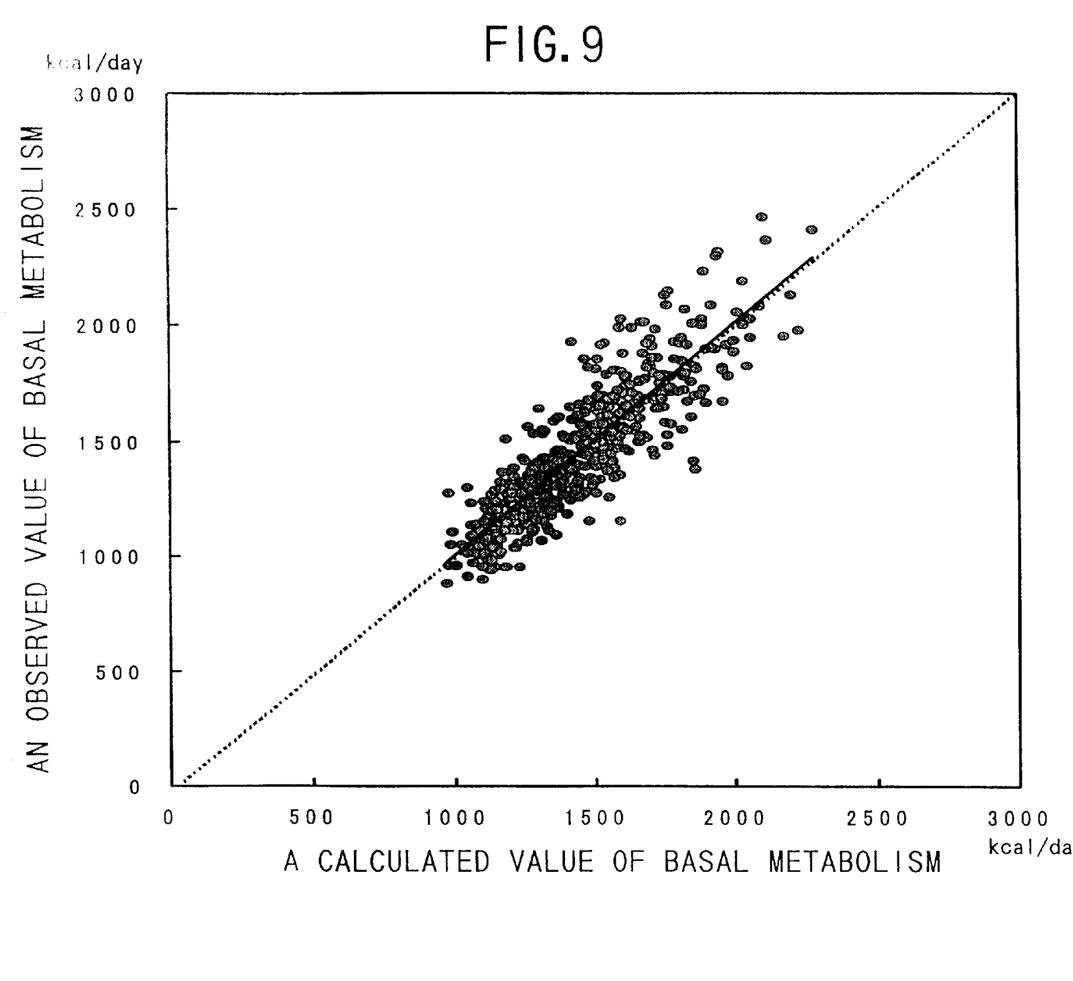
FIG. 9 is a graph showing a relationship between a calculated value of basal metabolism and an observed value of basal metabolism.

As shown in FIG. 9, a correlation coefficient between the basal metabolism obtained using the above mentioned formula and the observed basal metabolism is 0.879. The observed value was obtained by analysis of expired gas. The difference between an observed value and a calculated value against fat-free mass is half of the data shown in FIG. 6.

As shown in FIG. 2, a calculated value of basal metabolism tends to be lower than an observed value thereof in human with extremely low fat-free mass. The inventors of the present invention have found that a reciprocal of an age and squared thereof in addition to fat-free mass should be paid is preferably utilized to calculate basal metabolism. Accordingly, the inventors have found that the basal metabolism can be calculated using the formula represented by $BMR = A \times FFM^2 + B \times FFM + C \times (1/age) + D \times body\ weight + E$, in which BMR is basal metabolism (kcal/day), FFM is fat-free mass (kg), and A, B, C, D, and E are constants. It should be understood, however, that the formula is not limited to using metric measuring system values and can use any type of measuring system values.

Figure 10:
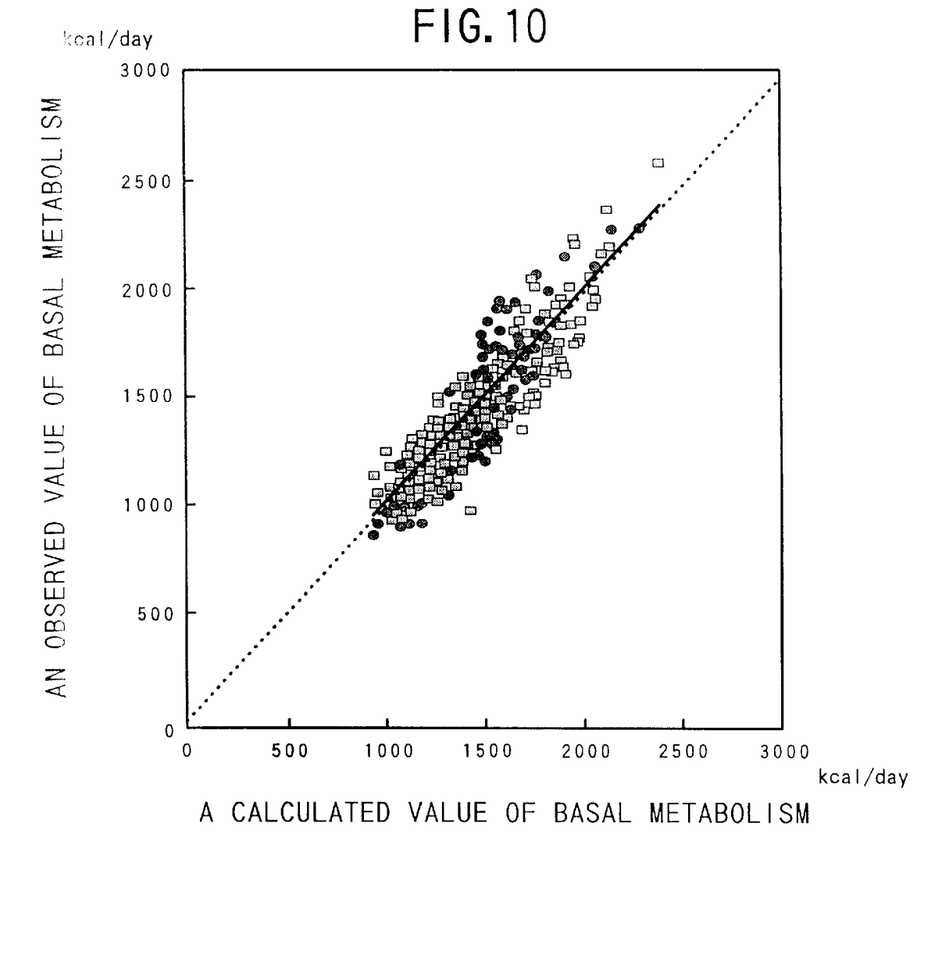
FIG. 10 is a graph showing a relationship between a calculated value of basal metabolism and an observed value of basal metabolism.

As shown in FIG. 10, a correlation coefficient between the basal metabolism obtained using the above mentioned formula and the observed basal metabolism is 0.88. The observed value was obtained by analysis of expired gas. The difference between an observed value and a calculated value against fat-free mass is substantially identical with the data shown in FIG. 8.

According to the above-described embodiment of the invention, values for fat-free mass, age, and body weight are required to calculate the basal metabolism. The basal metabolism can therefore be determined, for example, by changing a control program of a commercially available body fat measuring apparatus attached with weighing machine or an body fat measuring apparatus in which a value of body weight is manually inputted. Any method of determining fat-free mass is acceptable for use with the invention, for example, a bio-electric impedance analysis method (BIA method), a DEXA method, a method using a caliper, and the like may be employed.

The present invention can be practiced by employing conventional methodology and equipment. Accordingly, the details of such equipment and methodology are not set forth herein in detail. In the previous descriptions, numerous specific details are set forth in order to provide a thorough understanding of the present invention. However, it should be recognized that the present invention can be practiced without resorting to the details specifically set forth. In other instances, well known processing structures or methods have not been described in detail, in order not to unnecessarily obscure the present invention.

Only the preferred embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. An arithmetic method for determining basal metabolism, comprising the steps of:

obtaining an age of a subject;

determining fat-free mass of the subject; and determining basal metabolism of the subject using the determined fat-free mass and a reciprocal of the age.

2. The invention according to claim 1, wherein the basal metabolism is calculated using a formula represented by $BMR = A \times FFM + B \times (1/age) + C$, wherein BMR is basal metabolism, FFM is fat-free mass, and A, B, and C are constants.

3. The invention according to claim 1, wherein the basal metabolism is calculated using a formula represented by $BMR = A \times FFM^2 + B \times FFM + C \times (1/age) + D$, wherein BMR is basal metabolism, FFM is fat-free mass, and A, B, C, and D are constants.

4. An arithmetic method for determining basal metabolism, comprising the steps of:

obtaining an age and a body weight of a subject;

determining fat-free mass of the subject; and determining basal metabolism of the subject using the determined fat-free mass, the body weight, and a reciprocal of the age.

5. The invention according to claim 4, wherein the basal metabolism is calculated using a formula represented by $BMR = A \times FFM + B \times (1/age) + C \times body\ weight + D$, wherein BMR is basal metabolism, FFM is fat-free mass, and A, B, C, and D are constants.

6. The invention according to claim 4, wherein the basal metabolism is calculated using a formula represented by $BMR = A \times FFM^2 + B \times FFM + C \times (1/age) + D \times body\ weight + E$ wherein BMR is basal metabolism, FFM is fat-free mass, and A, B, C, D, and E are constants.

* * * * *